United States Patent [19]

Weaver

[11] 4,438,088

[45] Mar. 20, 1984

[54] PREPARATION OF ANTIMONY TRIFLUORODICHLORIDE AND FLUORINATION OF FLUORINATABLE HYDROCARBONS AND HALOCARBONS THEREWITH

[75] Inventor: John D. Weaver, Lake Jackson, Tex.

[73] Assignee: The Dow Chemical Company, Midland, Mich.

[21] Appl. No.: 357,342

[22] Filed: Mar. 11, 1982

[51] Int. Cl.³ .............................................. C01B 7/24
[52] U.S. Cl. ................................... 423/466; 570/144; 570/145; 570/154; 570/160; 570/170; 570/175
[58] Field of Search ............... 570/144, 145, 154, 160, 570/170, 175; 423/466, 87; 252/441

[56] References Cited

U.S. PATENT DOCUMENTS

| | | | |
|---|---|---|---|
| 1,930,129 | 4/1930 | Midgley et al. | 570/170 |
| 1,984,480 | 12/1934 | Henne | 423/466 |
| 2,013,050 | 9/1935 | Henne | 570/170 |
| 2,787,646 | 4/1957 | Hazeldine | 570/160 |
| 4,078,007 | 3/1978 | Ferstandig | 570/170 |

*Primary Examiner*—Edward J. Meros
*Assistant Examiner*—Robert L. Stoll
*Attorney, Agent, or Firm*—Norman L. Sims; Douglas N. DeLine

[57] ABSTRACT

The invention disclosed herein is a method for preparing antimony trifluorodichloride whereby antimony trifluoride is dispersed in a liquid organic medium to form a slurry and contacted with chlorine. The invention further comprises a process for fluorinating a fluorinatable hydrocarbon or halocarbon whereby a fluorinatable hydrocarbon or halocarbon is contacted with the antimony trifluorodichloride prepared in the above process, and the fluorinated product is distilled off.

16 Claims, No Drawings

PREPARATION OF ANTIMONY TRIFLUORODICHLORIDE AND FLUORINATION OF FLUORINATABLE HYDROCARBONS AND HALOCARBONS THEREWITH

BACKGROUND OF THE INVENTION

This invention involves a novel process of making antimony trifluorodichloride and using it to fluorinate a fluorinatable hydrocarbon or halocarbon in one reaction vessel. Antimony trifluorodichloride is an extremely effective agent for the exchange of fluorine atoms for other halogen atoms on aliphatic hydrocarbons. See Henne, U.S. Pat. No. 1,978,840.

It is already known to prepare antimony trifluorodichloride by reacting antimony trifluoride and antimony pentachloride as disclosed by F. Swartz, *Bull. Acad. Roy. Belg.*, 3 (24), p 474 (1892).

Daudt et al., in U.S. Pat. No. 2,005,705, disclosed the reaction of antimony pentachloride with hydrogen fluoride, and Dehnicke et al., *Z. Anorg. Allgem. Chem.*, 323, 267–74 (1963) (CA 59:12300n), taught a process of reacting $ClF_3$ and antimony pentafluoride in the presence of excess chlorine.

It is also known to prepare antimony trifluorodichloride from antimony trifluoride by contacting the solid reactant with gaseous chlorine in the absence of a liquid reaction medium. In this process, disclosed by A. Henne, *Organic Reactions*, 2, 49 (1944), solid antimony trifluoride is charged to a high pressure steel cylinder. The cylinder is then sealed, evacuated and chlorine in molar ratios of 5 to 100 percent of the antimony trifluoride is added. The cylinder must be heated and cooled for the antimony trifluorodichloride, a viscous liquid, to flow and expose fresh surfaces of antimony trifluoride. Occasional rolling of the cylinder helps to expose fresh surfaces of antimony trifluoride. The antimony trifluorodichloride from this process is extremely viscous and cannot be easily poured from the reaction flask. Further, due to the low available surface area at which chlorine may react with antimony trifluoride and the disparate phases of the two reactants, the reaction is extremely slow and not all of the antimony trifluoride is consumed even in the presence of excess chlorine.

In Henne, U.S. Pat. No. 1,984,480, antimony trifluoride was contacted with chlorine in the presence of either liquid antimony trichloride or antimony pentachloride, thereby producing a mixture of antimony trifluorodichloride and antimony pentachloride. As a fluorinating agent, the mixture thus produced is not as effective as antimony trifluorodichloride alone. A difficult to perform distillation of the binary mixture is therefore required in order to provide a suitably pure form of antimony trifluorodichloride.

It would be desirable to provide a method whereby antimony trifluorodichloride is prepared expeditiously, in high purity free of additional halogenated antimony compounds and in a manner easily adapted to further employ the antimony trifluorodichloride as a fluorinating agent.

SUMMARY OF THE INVENTION

The invention disclosed herein is a method for preparing antimony trifluorodichloride whereby antimony trifluoride is dispersed in a liquid organic medium to form a slurry and contacted with chlorine. The invention further comprises a process for fluorinating a fluorinatable hydrocarbon or halocarbon whereby a fluorinatable hydrocarbon or halocarbon is contacted with the antimony trifluorodichloride prepared in the above process, and the fluorinated hydrocarbon or halocarbon product is distilled off.

DETAILED DESCRIPTION OF THE INVENTION

According to the invention, antimony trifluoride in the form of a dry, finely powdered solid, is dispersed in the organic liquid medium so as to create a slurry. The slurry is then contacted with chlorine, which is best introduced in gaseous form. After the reaction has gone to completion, a liquid phase of antimony trifluorodichloride is formed which is insoluble in the liquid organic medium. This allows easy separation of antimony trifluorodichloride from the liquid organic medium by decanting.

The medium in which the antimony trifluoride is dispersed may be any organic liquid. Preferably, the liquid organic medium has a boiling point of above about 50° C., more preferably above about 90° C. and most preferably above about 150° C. The liquid organic medium is preferably a fluorinatable hydrocarbon, a fluorinatable halocarbon or an inert organic liquid, such as a perfluorocarbon.

Chlorine is added to the slurry up to an amount equimolar to the antimony trifluoride. As more chlorine is added to the antimony trifluoride, the product becomes a stronger fluorinating agent until the product is pure antimony trifluorodichloride. Chlorine in excess of this amount will not adversely effect the reaction.

During the chlorination of the antimony trifluoride it is not necessary to heat the reaction mixture, but without doing so the reaction goes very slowly. The reaction starts faster if the temperature is raised to between about 50° C. to 150° C., preferably 70° C. to 130° C., most preferably 70° C. to 90° C. Since the reaction is exothermic, heating can be stopped and cooling may be required once the reaction has started.

Pressure does not affect the reaction significantly, thus the process may be run at any pressure including atmospheric pressure. The process can be done in any dry atmosphere which does not interfere with the reaction and is best done under an inert gas atmosphere, such as nitrogen.

One of the uses for antimony trifluorodichloride is as a fluorinating agent. This invention includes a process for fluorinating a fluorinatable hydrocarbon or halocarbon comprising contacting chlorine with antimony trifluoride dispersed in a liquid organic medium to prepare antimony trifluorodichloride and thereafter contacting the antimony trifluorodichloride with a fluorinatable hydrocarbon or halocarbon.

The fluorinatable hydrocarbon or halocarbon can be contacted with the antimony trifluorodichloride in several ways. The antimony trifluorodichloride may be decanted from the liquid organic medium and then contacted with the fluorinatable hydrocarbon or halocarbon. Alternatively, the fluorinatable hydrocarbon or halocarbon can be added to the reaction vessel in which the antimony trifluorodichloride is made. The latter is the preferred method of contacting. If the fluorinatable hydrocarbon or halocarbon is a liquid it may be added to the reaction vessel at any point in the process for making the antimony trifluorodichloride, or the fluorinatable hydrocarbon or halocarbon can be the liquid organic medium into which the antimony trifluoride is dispersed prior to chlorination.

If the fluorinatable hydrocarbon or halocarbon is a solid, it can be added to the reaction mixture at any time before, during or after the preparation of the antimony trifluorodichloride.

Once the fluorinatable hydrocarbon or halocarbon and the antimony trifluorodichloride have been contacted, the mixture is heated to the temperature at which the fluorinated product distills. Preferably, the temperature at which the fluorinated product distills is less than 150° C. as the antimony trifluorodichloride decomposes at that temperature. The fluorinated product is separated from the reaction mixture by distilling the reaction mixture and collecting the vaporized product. The distillate is usually contaminated with small amounts of antimony salts, chlorine, hydrogen chloride or hydrogen fluoride. The product is usually washed and dried and if necessary, it may be purified, for example, by distillation.

The hydrocarbon or halocarbon which is fluorinated by this process can be any fluorinatable hydrocarbon or halocarbon. These fluorinatable hydrocarbons or halocarbons can be represented by the formulas:

$$R_3CX, R_2CX_2 \text{ and } RCX_3$$

wherein:
R is independently in each occurrence hydrogen, fluorine, phenyl, $C_1$–$C_{10}$ alkyl, $C_{1-10}$ alkenyl or halo-substituted derivatives thereof; and
X is selected from the group consisting of bromine, iodine, and chlorine.

These reactions involve the exchange of one or more fluorine atoms with one or more of the halogen atoms included in the group represented by X. The relative reactivity of the halogen is affected by the atoms attached to the same and adjacent carbon atoms. $CX_3$ groups are the most reactive and —$CX_2$— groups are quite reactive. $CHX_2$ reacts more slowly with fluorine and $CH_2X$ and —CHX— groups are not affected by a fluorine exchange reaction. In most instances, side reactions and decompositions increase as the hydrogen content of the molecule increases.

Halocarbons are alkanes or alkenes saturated with halogen atoms and are particularly fluorinatable and are preferred starting compounds; examples are perchloroethane and perchloropropane. These preferred fluorinatable halocarbons include alkanes or alkenes completely substituted with halogen atoms including one or more fluorine atoms, for example, 2-fluoroheptachloropropane.

The proportions of reactants are not critical. Where the fluorination is done in the same reactor as the preparation of antimony trifluorodichloride, the amount of antimony trifluoride used depends upon the equivalents of fluorine to be added to the fluorinatable hydrocarbon or halocarbon product. At least 0.33 mole of antimony trifluoride should be used for each equivalent of fluorine to be added to the fluorinatable hydrocarbon or halocarbon. The optimum ratio of antimony trifluoride to fluorinatable hydrocarbon or halocarbon is 0.5 mole of antimony trifluoride to 1.0 mole of fluorinatable hydrocarbon or halocarbon for each equivalent of fluorine to be added to the fluorinatable hydrocarbon or halocarbon. This is because the last equivalent of fluorine in the antimony compound is the slowest to react.

This process will usually give a yield of over 80 percent of the desired product.

This process has several advantages over the prior art processes. Antimony trifluorodichloride is produced in a faster and simpler manner than in the prior art methods, and is obtained in a more usable form, in that the compound which is being fluorinated can be in the same reaction vessel in which the antimony trifluorodichloride is being made, or the antimony trifluorodichloride can easily be separated from the mixture for other uses because of the formation in an insoluble phase. The antimony trifluorodichloride can be made and used for fluorination in a glass or metal reaction vessel at atmospheric pressure. Another advantage is the absence of undesirable side products such as hydrogen chloride or hydrogen fluoride. A further advantage is that the antimony trifluorodichloride may be recovered by decanting it from the reaction vessel free from undesirable antimony halide contaminants.

Trivalent and pentavalent antimony halides and mixtures thereof are commonly used for fluorine replacement of other halogens. The particular antimony halide or mixture of antimony halides chosen for a fluorination reaction depends upon the ease of replacement of the halogens desired to be replaced. The relative fluorination power of antimony halides is

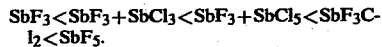
$SbF_3 < SbF_3 + SbCl_3 < SbF_3 + SbCl_5 < SbF_3Cl_2 < SbF_5$.

$SbF_3Cl_2$ should be chosen to fluorinate those fluorinatable hydrocarbons or halocarbons which are defined above.

The practice of the instant invention is further illustrated by the following examples. These embodiments and examples are not intended to limit the scope of the instantly claimed invention.

EXAMPLE 1

Preparation of 1,2,3-Trichloropentafluoropropane

A 1000-ml three-neck flask equipped with a mechanical stirrer, a gas entry tube and a dry ice condenser, was charged under nitrogen with 500 g (1.65 moles) of 2-fluoroheptachloropropane and 590 g (3.30 moles) of antimony trifluoride. The slurry was stirred vigorously and heated as chlorine was distilled into the flask. After about 10 minutes when an excess of unreacted chlorine had accumulated and the temperature had reached 80° C., the reaction started to proceed very quickly. The unreacted chlorine suddenly disappeared and heat was evolved. The heating mantle was removed and the reaction rate was controlled by the rate of addition of chlorine, since it was consumed as fast as it was added. The temperature of the slurry reached 90° C.–100° C. After about 1 hour, chlorine began to reflux on the condenser. The addition was stopped and the slurry, now light brown in color, was allowed to cool. It was determined that 247 g (3.48 moles) of chlorine had been added. The slurry was believed to contain 3.30 moles of antimony trifluorodichloride. The condenser was replaced with a distillation column and the product was distilled from the reactor as it was formed while the slurry was heated to 105° C.–130° C. The reaction and concurrent distillation was continued until no more product was obtained. After it was washed, dried and distilled, there was obtained 328 g (84 percent yield) of 1,2,3-trichloropentafluoropropane.

EXAMPLE 2

Preparation of 1,2,3-Trichloropentafluoropropane

A 5-liter flask was equipped with an efficient mechanical stirrer, a thermometer, a gas entry tube and a distillation head connected to a dry nitrogen source. The flask was charged with 3880 g (12.8 moles) of 2-fluoroheptachloropropane and 4575 g (25.6 moles) of antimony trifluoride.

The mixture was warmed to 80° C. and addition of chlorine was begun. The heat of reaction caused the temperature to rise to about 115° C. during the addition. When the temperature began to drop again, chlorine addition was stopped. The mixture was heated to about 110° C. and the fluorinated organic product was distilled from the reactor as it was formed. 1,2,3-Trichloropentafluoropropane (2130 g, 70 percent yield) was collected at b.p. 70° C.–75° C.

EXAMPLE 3

Preparation of 1,1,2-Trichlorotrifluoroethane from Solid Hexachloroethane

A 250-ml four-neck flask, equipped with a mechanical stirrer, a thermometer, a gas entry tube and a dry ice condenser, is charged under nitrogen with 107 g (600 mmoles) of antimony trifluoride and 75 ml of perfluorodecalin. The slurry is warmed to about 80° C. and while it is stirred briskly, 42 g (600 mmoles) of chlorine is added at such a rate that the temperature of the slurry remains below 100° C.

When all of the chlorine has reacted, the resulting mixture of antimony trifluorodichloride and perfluorodecalin is cooled to room temperature and 95 g (400 mmoles) of hexachloroethane are added. The condenser is replaced with a distillation head and the slurry is heated with stirring. 1,1,2-Trichlorotrifluoroethane is collected at b.p. 46° C.–48° C.

EXAMPLE 4

Preparation of 1,2,2,3-Tetrachlorotetrafluoropropane from Solid Perchloropropane A slurry of antimony trifluorodichloride (600 mmoles) in 75 ml of perfluorodecalin is prepared as described in Example 3. To this is added perchloropropane (96 g, 300 mmoles) and the mixture is heated as before. 1,2,2,3-Tetrachlorotetrafluoropropane is distilled from the reaction at b.p. 110° C.–112° C.

What is claimed is:

1. A process for making antimony trifluorodichloride comprising dispersing antimony trifluoride in a liquid organic medium and contacting the dispersed antimony trifluoride with an amount of chlorine up to an amount equimolar to the antimony trifluoride, wherein the liquid reaction organic medium is selected from a group consisting of fluorinatable hydrocarbons, fluorinatable halocarbons and perfluorocarbons, under conditions such that antimony trifluorodichloride is prepared.

2. A process for making antimony trifluorodichloride comprising dispersing antimony trifluoride in a liquid organic medium and contacting chlorine with the dispersed antimony trifluoride at a temperature of between about 50° C. and 150° C.; wherein the amount of chlorine is up to that amount equimolar to the antimony trifluorodichloride; and wherein the liquid organic reaction medium is a fluorinatable hydrocarbon or a fluorinatable halocarbon, under conditions such that antimony trifluorodichloride is prepared.

3. The process of claim 2 wherein the dispersion is initially heated to between about 70° C. and 130° C. when the chlorine is added.

4. The process of claim 2 wherein the dispersion is initially heated to between about 70° C. and 90° C. when the chlorine is added.

5. A process for fluorinating a fluorinatable hydrocarbon or halocarbon comprising contacting chlorine with antimony trifluoride dispersed in a liquid organic medium to prepare antimony trifluorodichloride and thereafter contacting antimony trifluorodichloride with a fluorinatable hydrocarbon or halocarbon, and distilling the fluorinated product from the reaction vessel, wherein the chlorination of the antimony trifluoride and the fluorination of the fluorinatable hydrocarbon or halocarbon occur in the same reaction vessel; and wherein the fluorinatable hydrocarbon or halocarbon can be represented by the formula

$$R_3CX, R_2CX_2 \text{ or } RCX_3$$

wherein

R is independently in each occurrence hydrogen, fluorine, phenyl, $C_{1-10}$ alkyl, $C_{1-10}$ alkenyl or halo-substituted derivatives thereof; and X is selected from the group consisting of bromine, iodine and chlorine.

6. The process of claim 5 wherein the fluorinatable halocarbon is an alkane or alkene which is saturated with halogen atoms.

7. The process of claim 6 wherein the fluorinatable halocarbon is perchloroethane and the fluorinated halocarbon product is 1,1,2-trichlorotrifluoroethane.

8. The process of claim 6 wherein the starting fluorinatable halocarbon is perchloropropane and the fluorinated product is 1,2,2,3-tetrachlorotetrafluoropropane.

9. The process of claim 6 wherein the fluorinatable halocarbon has one or more fluorine atoms.

10. The process of claim 9 wherein the starting fluorinatable halocarbon is 2-fluoroheptachloropropane and the fluorinated product is 1,2,3-trichloropentafluoropropane.

11. The process of claim 10 whereby the two-phase system is heated to a distillation head temperature of between about 70° C. and 80° C.

12. The process of claim 5 wherein the liquid organic medium is a fluorinatable hydrocarbon or halocarbon.

13. The process of claim 5 wherein the fluorinatable hydrocarbon or halocarbon is a solid which is added to the liquid organic medium.

14. A process for the preparation of antimony trifluorodichloride and use of antimony trifluorodichloride to fluorinate a fluorinatable hydrocarbon or a fluorinatable halocarbon wherein the process comprises, (1) dispersing antimony trifluoride in a fluorinatable hydrocarbon, fluorinatable halocarbon or a liquid organic reaction medium wherein a fluorinatable hydrocarbon or fluorinatable halocarbon has been dissolved in the liquid organic reaction medium, to form a slurry and contacting chlorine with the dispersed antimony trifluoride under conditions such that antimony trifluorodichloride is prepared; and (2) recovering the fluorinated hydrocarbon or fluorinated halocarbon product.

15. The process of claim 14 wherein the fluorinated hydrocarbon or fluorinated halocarbon is recovered by elevating the temperature to that at which the fluorinated hydrocarbon or fluorinated halocarbon distills, and by collecting and condensing the vaporous product.

16. The process of claim 15 wherein the antimony trifluorodichloride is dispersed in a fluorinatable hydrocarbon or fluorinatable halocarbon.

* * * * *